United States Patent [19]

Warner et al.

[11] Patent Number: 5,364,392
[45] Date of Patent: Nov. 15, 1994

[54] MICROWAVE ABLATION CATHETER SYSTEM WITH IMPEDANCE MATCHING TUNER AND METHOD

[75] Inventors: Glen G. Warner, Morgan Hill; David A. Grundy, Fremont, both of Calif.

[73] Assignee: Fidus Medical Technology Corporation, Fremont, Calif.

[21] Appl. No.: 62,637

[22] Filed: May 14, 1993

[51] Int. Cl.⁵ .............................................. A61B 17/39
[52] U.S. Cl. .......................................... 606/34; 606/33; 606/38; 607/101; 607/154; 607/156
[58] Field of Search .............. 607/101, 102, 115, 116, 607/154, 122; 606/32–34, 37, 38, 41, 42, 45, 46

[56] References Cited

U.S. PATENT DOCUMENTS

| | | | |
|---|---|---|---|
| 4,244,371 | 1/1981 | Farin | 606/35 |
| 4,416,276 | 11/1983 | Newton et al. | 606/35 |
| 4,494,539 | 1/1985 | Zenitani | 606/34 |
| 4,657,015 | 4/1987 | Imich | 606/35 |
| 4,945,912 | 8/1990 | Langberg . | |
| 5,019,076 | 5/1991 | Yamanashi et al. | 606/45 |
| 5,150,717 | 9/1992 | Rosen et al. | 606/33 |
| 5,188,122 | 2/1993 | Phipps et al. | 606/33 |

Primary Examiner—Stephen C. Pellegrino
Assistant Examiner—Michael Peffley
Attorney, Agent, or Firm—Hickman & Beyer

[57] ABSTRACT

A tuner system for a microwave power supply used in an ablation catheter system is disclosed. The tuner system includes a tuner arranged to facilitate matching the impedance of a power generator side portion of the catheter system with the impedance of a catheter side portion of the catheter system. A reflected power monitor is also provided for monitoring the amount of power that is reflected from the catheter during use. In a preferred aspect of the invention, the tuner is used in a power supply that includes a microwave power source and is used in conjunction with a catheter having a coaxial transmission line and a helical antenna. In a method aspect of the invention, a method for medical treatment using a microwave ablation catheter system is disclosed.

12 Claims, 7 Drawing Sheets

MICROWAVE ABLATION CATHETER SYSTEM WITH IMPEDANCE MATCHING TUNER AND METHOD

BACKGROUND OF THE INVENTION

The present invention relates generally to ablation catheter systems that use electromagnetic energy in the microwave frequencies to ablate internal bodily materials. More particularly, a microwave power supply for use in conjunction with an ablation catheter is disclosed which includes a tuner for impedance matching of the power supply and catheter microwave transmission line components in order to minimize reflected power and maximize catheter to tissue coupling.

Catheter ablation has recently become an important therapy for selected patients with certain arrhythmias. Two of the most common ablation approaches are: 1) to use high voltage, direct current defibrillator discharges; and 2) to use radio frequency (RF) energy as the ablating energy source. Direct current ablation has several drawbacks including the need for general anesthesia and explosive discharges leading to dangerous barotrauma effects. The problem with RF energy is that the lesion size is limited. Accordingly, in order to ablate sufficient cardiac tissue to perform the operation, it is often necessary to make repeated lesions. Although this is not necessarily dangerous, it is inefficient and often unsuccessful.

In view of the drawbacks of the traditional catheter ablation techniques, there has recently been an interest in using microwave energy as an ablation energy source. The advantage of microwave energy is that it is much easier to control and safer than direct current applications and it is capable of generating substantially larger and deeper lesions than RF catheters, which greatly simplifies the actual ablation procedures, and increases versatility by allowing treatment of supra ventricular and other previously inaccessible arrhythmogenic tissues.

In U.S. Pat. No. 4,641,649, Walinsky et al. disclose a medical procedure for the treatment of tachycardia and cardiac disrhythmia which uses microwave frequency electrical energy to ablate selected cardiac tissue. The microwave energy is transmitted over a coaxial transmission line having an antenna at its distal end. A procedure is disclosed in Langberg et al's article entitled "Catheter Ablation of the Atrioventricular Junction Using a Helical Microwave Antenna: A Novel Means of Coupling Energy to the Endocardium," *PACE*, pp. 2105-2113 Vol. 14 (1991). As suggested in the title, the Langberg et al. article proposes the use of a helical microwave antenna at the distal end of the catheter in order to improve the catheter's power delivery characteristics. Both of these disclosures discuss potential uses of microwave based ablation catheters and are incorporated herein by reference.

In coronary applications such as those discussed in the Walinsky and Langberg references, the catheter diameter is typically limited to approximately 7½ French (approximately 2.5 mm in diameter). One problem that arises when using the very small diameter transmission lines that are necessitated by such diameter limitations is that the attenuation is quite large over the length of the transmission line. More troublesome is that during use, this attenuation can result in significant heat generation in the transmission line and catheter. Also of significant challange is that the impedance of the catheter to tissue coupling will vary with the location at which the catheter tip is placed in the heart. During the course of a typical ablation procedure, tissue changes and heating of the transmission line components will also effect the impedance of the catheter as viewed by the power supply.

In a typical microwave ablation catheter system, it is important to match the impedance on the catheter side with the impedance on the microwave generator side. However, the impedance on the catheter side tends to vary a fair amount as the catheter is moved about during use and as tissue properties change during an ablation procedure. This is generally due to a combination of several factors, the most notable of which seem to include heating within the catheter and changes induced as the target tissue is ablated. When the impedance changes, an increased percentage of the power is reflected and the catheter's performance is reduced. By way of example, in a representative application wherein the transmission line is approximately one meter long and is a coaxial transmission line having a diameter of 72 thousandths of an inch (1.8 mm), the power output of a well tuned system may only be in the range of 25-30% of the input power. Of course, the power output is likely to improve as the technology develops, but attenuation is always likely to be a significant concern.

SUMMARY OF THE INVENTION

Accordingly, it is an object of the present invention to provide a tuner for a microwave ablation catheter system that matches the impedance between the microwave generator side and the catheter side of the system in real time.

To achieve the foregoing and other objects and in accordance with the purpose of the present invention, a tuner system for a microwave power supply used in an ablation catheter system is disclosed. The tuner system includes a tuner arranged to facilitate matching the impedance of a power generator side portion of the catheter system with the impedance of a catheter side portion of the catheter system. A reflected power monitor is also provided for monitoring the amount of power that is reflected from the catheter during use. In a preferred embodiment, the reflected power monitor includes a directional coupler and a power sensor. In another preferred embodiment, the tuning system further includes a tuner controller that receives a signal indicative of the magnitude of the reflected power from the reflected power monitor and generates a control signal based at least in part on the magnitude of the reflected power to automatically match the impedance of the power supply side portion of the catheter system with the catheter side portion of the catheter system. In yet another preferred embodiment, the tuner takes the form of a stub tuner.

In a preferred embodiment, the tuner system is used in a power supply that includes a microwave generator, and an interlock system for automatically shutting off the microwave generator when certain predefined safety hazards are detected. Representative safety hazards may include when no catheter is plugged into the power supply, when the catheter tip is damaged, and/or when a thermometry component is damaged or when excessive temperatures are detected in the catheter or tissues.

In another preferred embodiment, the power supply is used with a microwave catheter having a coaxial transmission line that serves as its waveguide. In a more preferred embodiment, the antenna is insulated and may take either a helical or alternative form.

In a method aspect of the invention, a method for medical treatment using a microwave ablation catheter system is disclosed. The method includes the steps of introducing a catheter having a waveguide and an antenna coupled to the distal end of the waveguide into a patient's body such that the antenna is positioned adjacent material to be ablated. The initial impedance of a catheter side portion of the ablation catheter system is then adjusted to balance the initial impedance of a power supply portion of the ablation catheter system. Microwave energy is applied to the waveguide using a microwave power source coupled to the catheter for a period of time to ablate material in the vicinity of the antenna. The relative impedance of the catheter side portion of the ablation catheter system and the power supply portion of the ablation catheter system are then adjusted during use in order to compensate for impedance variations that occur during use of the catheter.

BRIEF DESCRIPTION OF THE DRAWINGS

The invention, together with further objects and advantages thereof, may best be understood by reference to the following description taken in conjunction with the accompanying drawings in which.

DETAILED DESCRIPTION OF THE INVENTION

Figure 1:
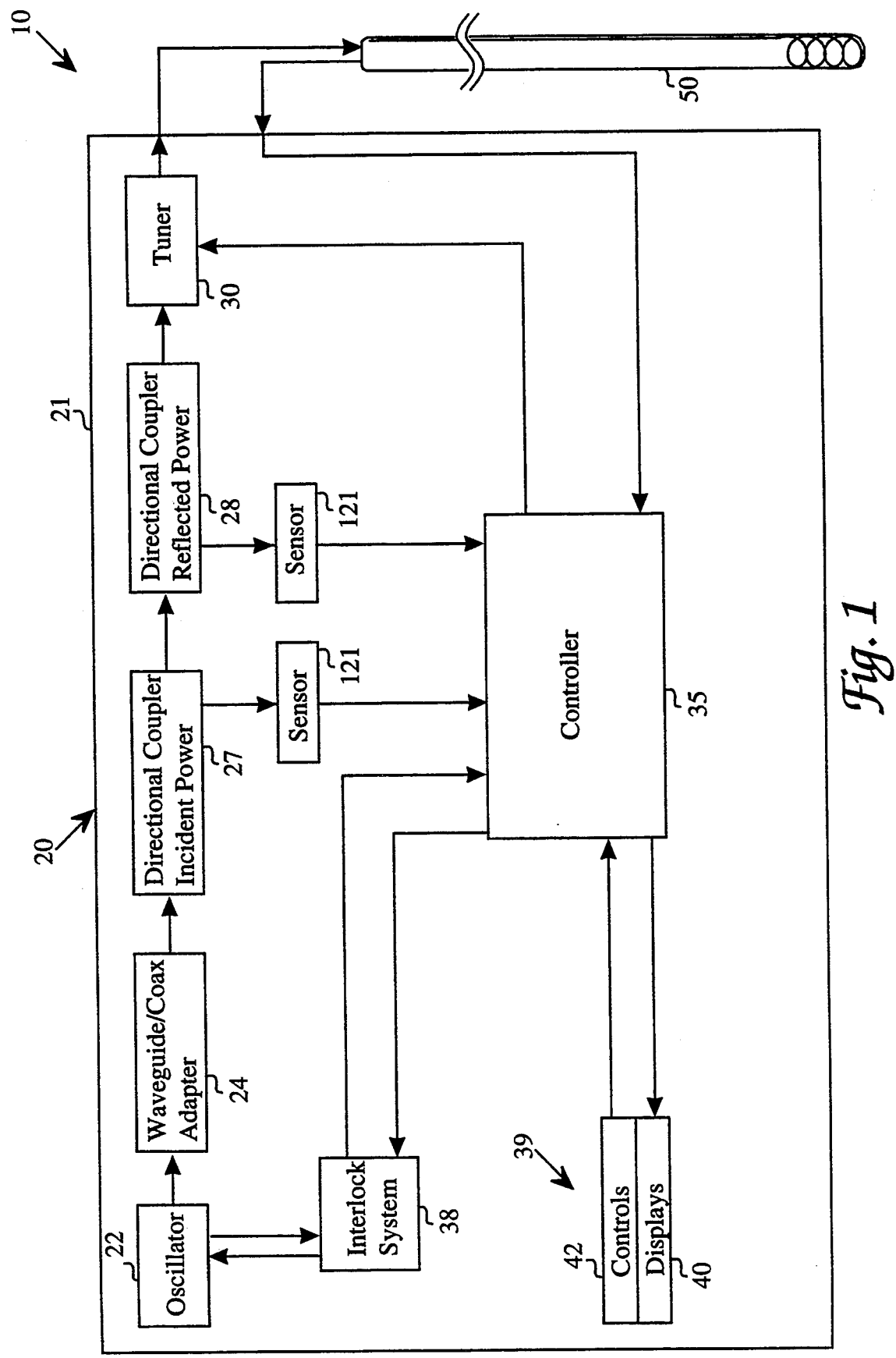
FIG. 1 is a schematic block diagram of a microwave power supply system for an ablation catheter in accordance with one embodiment of the present invention.

A presently preferred embodiment of an ablation catheter system in accordance with the present invention will be described below making reference to the accompanying drawings. As seen in FIG. 1, the ablation catheter system 10 generally includes a power supply 20 which is designed to generate controlled microwave energy, a catheter 50 which is designed for insertion into the body of a patient and a connector 90 for coupling the power supply 20 to the catheter 50. The power supply 20 includes a casing 21 having a microwave generator 22, a waveguide adapter 24, a pair of directional couples 27 & 28 that interface with power monitors 121, a tuner 30, a controller 35 and an interlock system 38 all enclosed therein. The front panel 39 of the casing has various displays 40 and controls 42.

The microwave generator 22 may take any conventional form. When using microwave energy for tissue ablation, the optimal frequencies are generally in the neighborhood of the optimal frequency for heating water. At the time of this writing, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz was chosen. At the time of this writing, solid state microwave generators in the 1–3 GHz range are very expensive. Therefore, a conventional magnetron of the type commonly used in microwave ovens was chosen as the generator. It should be appreciated, however, that any other suitable microwave power source could be substituted in its place.

At the time of this writing the best small diameter waveguides for transmitting microwave energy are transmission lines that take the form of coaxial cables. Thus, a conventional waveguide adapter 24 couples the microwave generator 22 to a coaxial cable. A pair of directional couplers 27 and 28, are provided downstream of the waveguide adapter 24. The output of each is coupled to a power sensor 121 whose signal is processed by the controller. Conventional power sensors may be used. The purpose of the directional coupler/power sensor arrangements is to monitor the power outputted by the generator 22 as well as the reflected power. In the described system, the first directional coupler 27/power sensor arrangement monitors the power output, while the second directional coupler 28/power sensor arrangement monitors the reflected power. It is contemplated that other suitable power monitors could be used in place of the described directional coupler/power sensor arrangements.

In coronary applications, the catheter diameter is limited to approximately 7½ French (approximately 2.5 mm in diameter). One problem that arises when using the very small diameter wave guides that are necessitated by such diameter limitations is that the attenuation is quite large over the length of the wave guide. By way of example, in a representative application wherein the wave guide is approximately one meter long coaxial transmission line having a diameter of 72 thousandths of an inch (1.8 ram), the power output of a well tuned system may only be in the range of 25–30% of the input power. Of course, the power output is likely to improve as the technology develops, but attenuation is always likely to be a significant concern.

In a typical microwave ablation catheter system, the system is designed to provide a set impedance. Although the actual set impedance may vary, a typical design impedance on the catheter side of the catheter system may be on the order of 50 ohms. However, the impedance tends to vary a fair amount as the catheter is moved about during use and as tissue properties change during ablation. This is true when helical antennas are used. The impedance variations have a number of sources, however a few of the items which have the greatest effect on impedance variations include the catheter tip location, patient to patient tissue variations, and temperature dependent dielectric properties of catheter components and patient tissues. When the impedance changes, the catheter's performance tends to be well below the optimal performance. The decline in performance is most easily seen in the increase in the reflected power. The tuner 30 is therefore provided to compensate for impedance variations that are seen by the power supply during use. In effect, the tuner manipulates the impedance of the catheter side of the catheter system. In the preferred embodiment shown in FIG. 2, the tuner 30 is a conventional stub tuner that has drive units that are arranged to move its stubs back and forth. In an alternative embodiment, the stubs may be manually adjusted by the user either directly (as seen in FIG. 3) or through manual control of the servos 119.

It should be appreciated that the tuner may take the form of mechanically adjustable waveguides or coaxial transmission line arrangements or they may be constructed of discrete component elements connected to the center conductor and outer shield of a coaxial transmission line. In the described embodiment, a coaxial transmission line mechanical tuner commonly referred to as a double stub tuner is used. By way of example, alternative embodiments may utilize a single stub tuner, a triple stub tuner, or a stub stretcher. Any of these tuners may be used in conjunction with a line stretcher to adjust the location of the tuner relative to the sources of the reflected power for further improving the impedance matching capability of the system.

In another alternative embodiment, the tuner may be incorporated into the antenna itself in the form of a mechanically adjustable antenna. By way of example, the helical antenna described below with reference to FIGS. 6 & 7 could readily be arranged in this manner. For example, a balloon mechanism, an expandable basket or other mechanical arrangements could be provided to compress the antenna in a spring like fashion.

The controller 35 may take the form of dedicated logic, but in a preferred embodiment a conventional microprocessor or computer is used. The controller 30 receives inputs from the sensors 121 coupled to directional couplers 27, 28 the catheter thermometry element 65, the interlock system 38 and the controls 42. If desired, the controller can also receive inputs from various other electrodes provided on the catheter and other controls. In the drawing shown in FIG. 1, the controller and interlock system are shown as two separate blocks. Although in a discrete logic system, they would typically include separate circuits, when a microprocessor is used as the controller, it can control the interlock system as well.

The interlock system 38 is intended to shut off the power supply any time it detects the occurrence of a potential problem. In the described embodiment, the interlock system detects: 1) an open casing for the power supply; 2) over heating of the microwave generator (this is unlikely to be a problem when the magnetron in the first described embodiment is used. The generator overheating interlock is more important in solid state systems); 3) overheating of the tissue or catheter elements; 4) when the catheter is damaged for any reason; and 5) when the catheter is not plugged into the power supply. Of course, the interlock system could be activated by a variety of other events as well.

Figure 6:
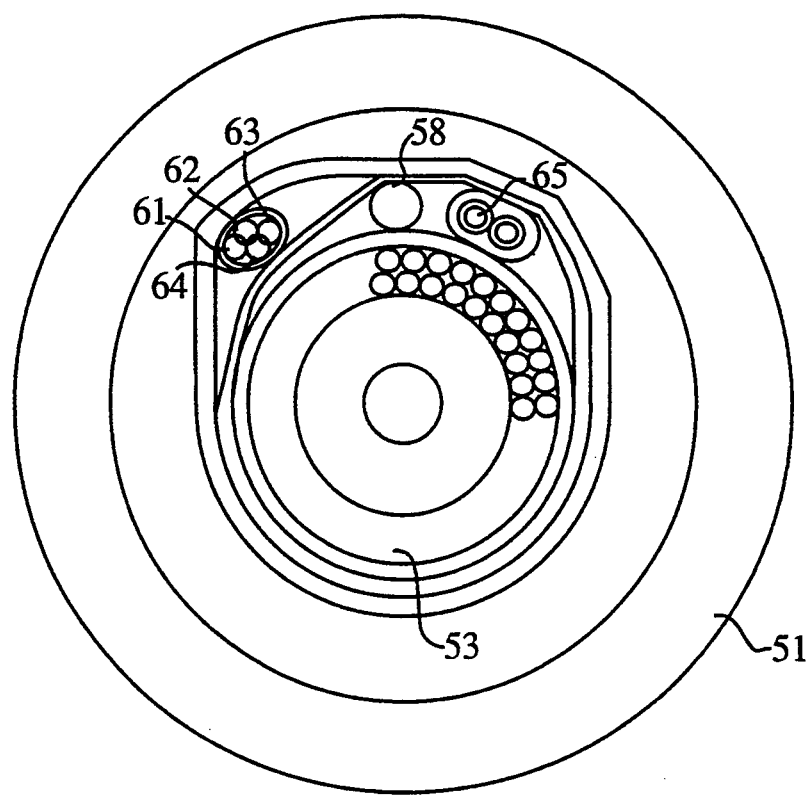
FIG. 6 is a cross sectional view of the ablation catheter shown in FIG. 5 taken along line 6—6.

By way of example, the open casing may be detected by a switch that is closed when the casing cover is secured. Overheating of the microwave generator may be detected by thermometry elements attached to the generator housing. Overheating of tissues or catheter elements is detected by thermometry element 65 (as seen in FIG. 6). Damage to the catheter may be detected as exceeding reflected vs. forward power boundary conditions or limits, sudden changes in reflected power or open circuit electrode, transmission line, or thermometry element conditions in the event of catastrophic damage.

The controller can also be programmed to test for sudden changes in a variety of signals in search of faults which warrant shutting down of the microwave generator. By way of example, sudden changes in the reflected power are often a sign of a dangerous conditions as catheter damage, coagulation, or excessive tissue damage. Tests for shorts or open circuits will indicate catastrophic catheter damage. Thus the controller 35 may be used as an integral part of the interlock system.

A power control switch 149 and a timer control 147 are each provided on the front panel 39 of the casing in order to permit the user (doctor) to control the power output. By way of example, in one described embodiment, the power control switch 43 permits the outputting of between 20 and 65 watts. The timer control switch 44 is provided to allow the user to control the length of the ablation procedure. Typical use times are up to approximately 100 seconds. Of course, this number may vary widely in accordance with the needs of a particular system.

Another safety feature is the reflected power display 46. If something happens to the catheter during use, the reflected power will increase dramatically. Thus, the reflected power display gives the doctor additional feedback which may indicate that a problem exists. A variety of other displays could be provided as well, such as remaining time display 48, temperature displays, impedance displays and any other suitable display.

Figure 2:
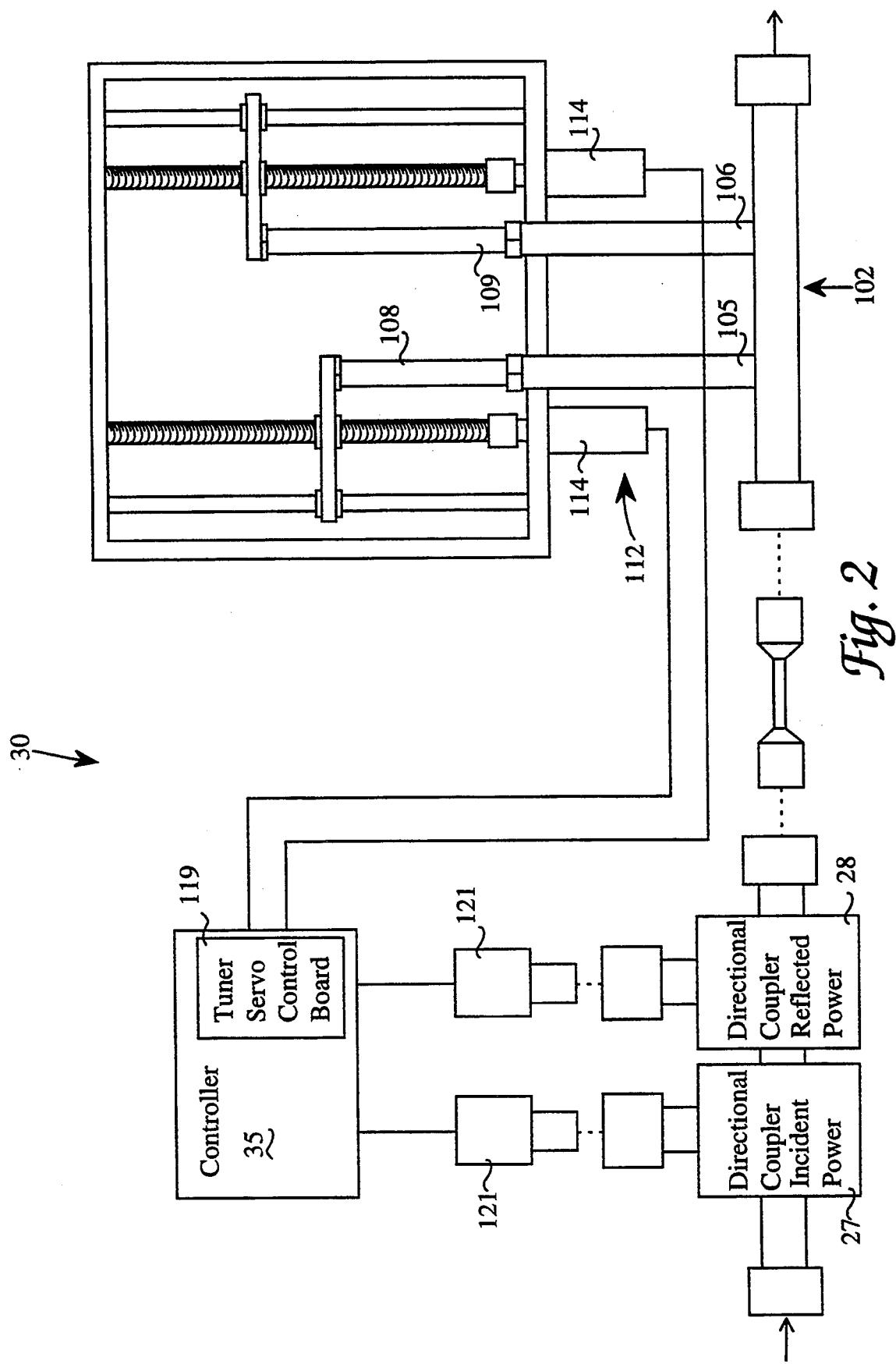
FIG. 2 is a schematic diagram of an automatic tuner system suitable for use in the ablation catheter power supply system shown in FIG. 1.
Figure 3:
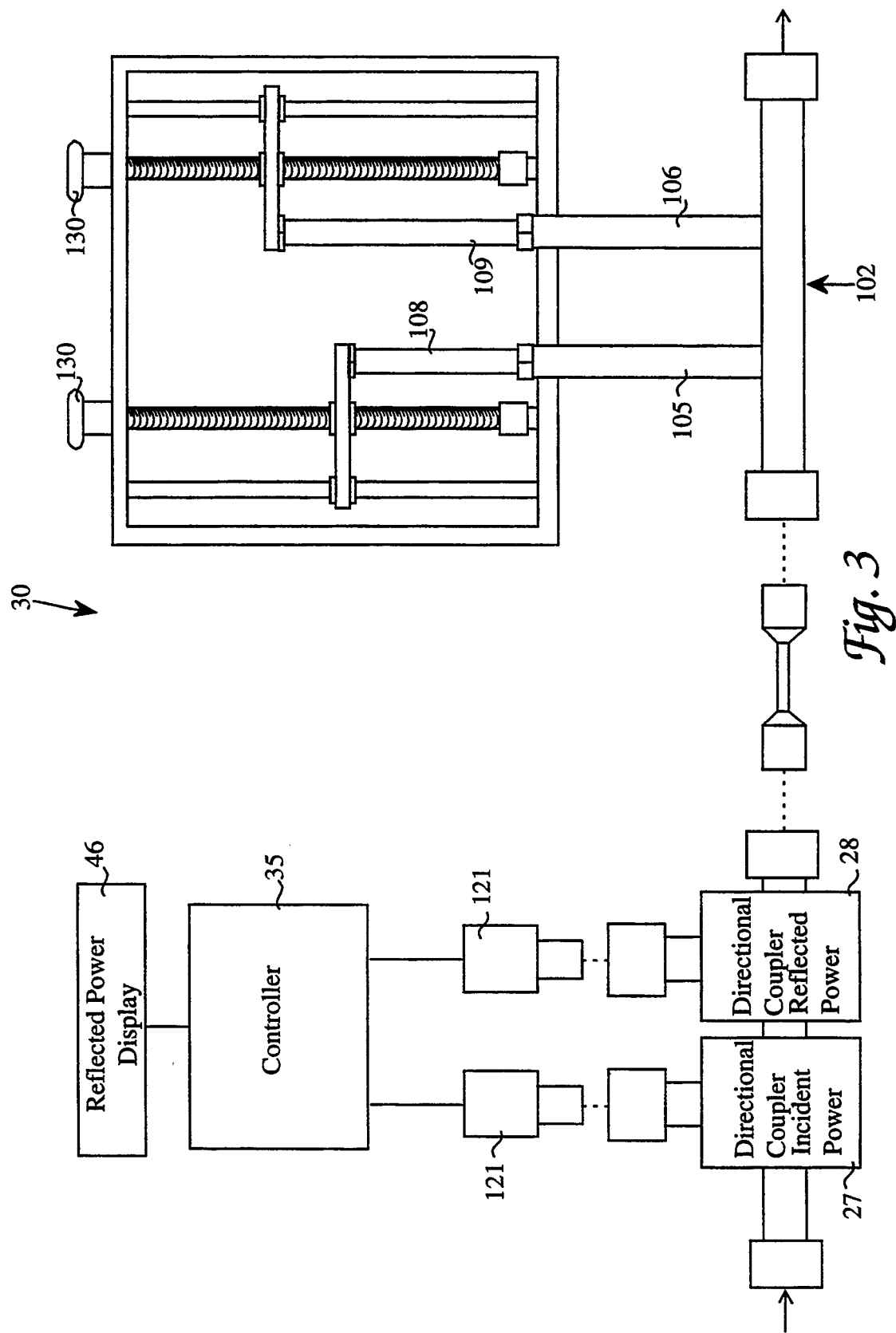
FIG. 3 is a schematic diagram of a manual tuner system suitable for use in the ablation catheter power supply system shown in FIG. 1.

Referring next to FIG. 2, a first embodiment of the tuner 30 will be described in more detail. In this embodiment of the tuner, an automatic feedback control is provided to minimize reflected power. A double stub tuner 102 is coupled on each end to coaxial cables which serve as the microwave waveguides. The stub tuner has a pair of stub arms 105, 106 which slidably receive plungers 108, 109 therein. A pair of motorized drive units 112 are provided with each drive unit 112 being associated with one of the plunger arms. Each drive unit 112 includes a motor 114, which can be controlled by controller 35. The controller 35 is arranged to receive a signal indicative of the magnitude of the reflected power from directional coupler 28. The controller will then adjust the tuning mechanism accordingly via a servo or stepper motor controller (119).

Referring next to FIG. 3, a manually adjusted version of the tuning system will be described. In this embodiment, a pair of adjustment knobs 130 are provided which allow the user to manually manipulate the plungers 108,109. The adjustment knobs 130 are mounted on the front display panel 39. In this case, the power sensor 121 again feeds the controller 35 which in turn provides a display signal to the reflected power display 46. The user can thus visually monitor variations in the reflected power and make suitable adjustments in the settings of the plungers of the stub tuner, thereby controlling the effective impedance of the catheter side of the ablation catheter system.

It is noted that in the described embodiments, the impedance variations are made on the catheter side of the system. That is, the portion of the system downstream from the tuner input. However, it should be appreciated that it would also be possible to make the changes on the microwave generator side, although this would likely not be as efficient. Of course, the ideal location of a tuner is at the site of the most significant discontinuity or mismatch, i.e. the distal end of the catheter.

Figure 4:
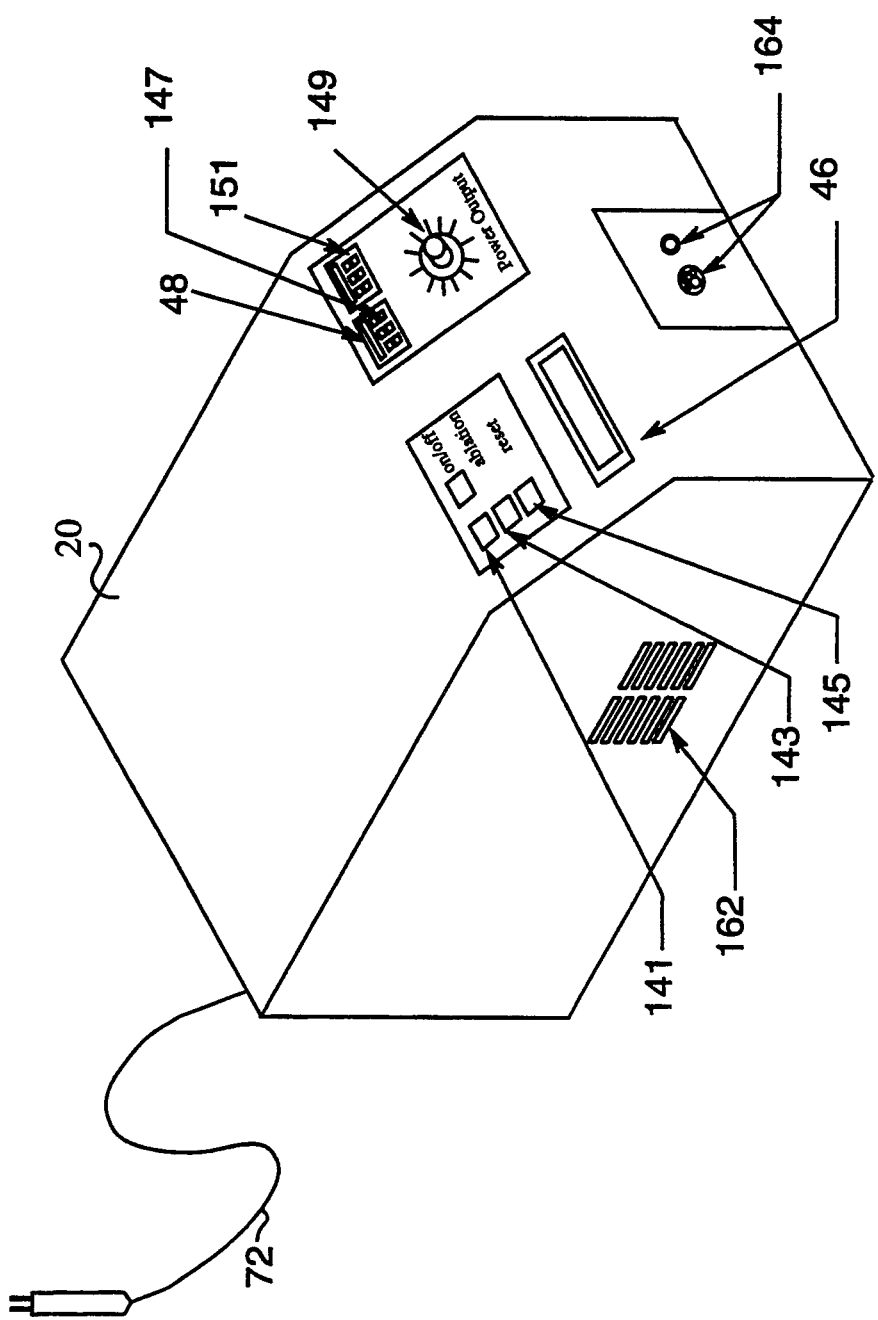
FIG. 4 is a schematic diagram of a display panel suitable for use in the ablation catheter power supply system shown in FIG. 1.

Referring next to FIG. 4, a representative display panel will be described. As seen therein, the display panel may include any number of suitable knobs and dials as for example, an on/off switch 141, an ablation start switch 143, a reset switch 145, a timer 147, and a power control dial 149. It may also include any number of suitable displays including by way of example, a reflected power display 46, a time display 48 and thermometry displays 151. In embodiments having a manually adjusted tuner, the adjustment knobs 130 may be provided as well. The power supply may also include air vents 162 for cooling and connectors 164 for coupling with the catheter and external electronics.

Figure 5:
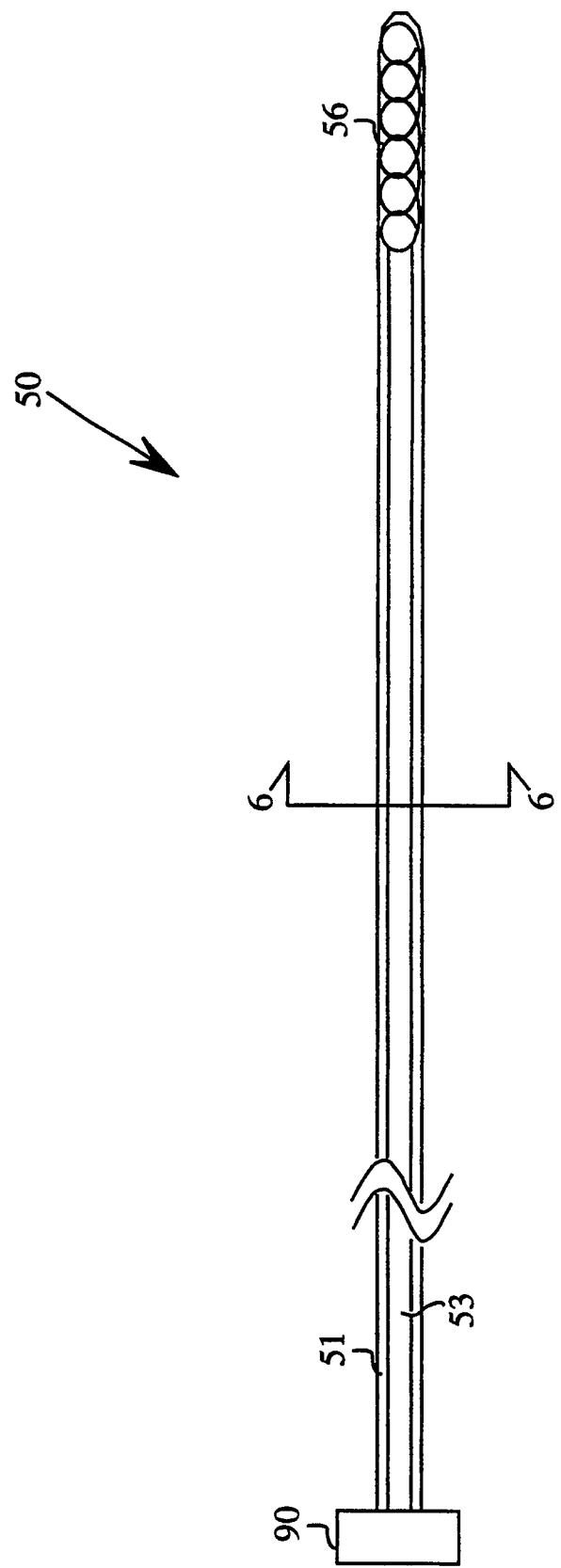
FIG. 5 is a diagrammatic side view of an ablation catheter suitable for use with the ablation catheter power supply system shown in FIG. 1.
Figure 7:
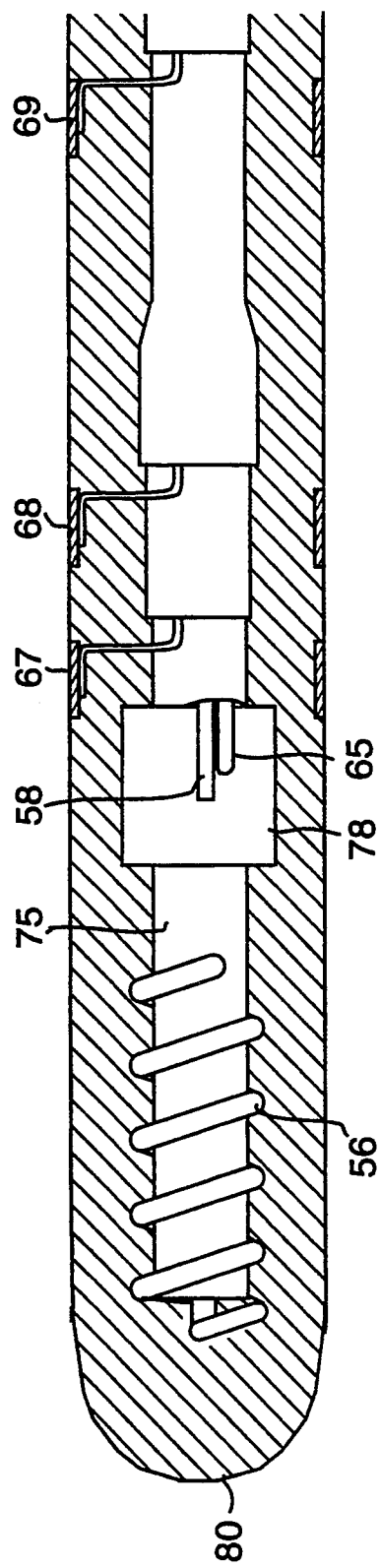
FIG. 7 is a enlarged diagrammatic side view of the antenna portion of the ablation catheter shown in FIG. 5.

Referring next to FIGS. 5–7, a suitable catheter for use in conjunction with the described power supply will be described. The catheter 50 includes outer tubing 51, a coaxial microwave transmission line 53, a helical antenna 56, a stiffener wire 58, a plurality of electrode wires 61–69, thermometry wires 65 which in this embodiment take the form of thermocouple wires 65 and electrodes 67–70. The outer tubing 51 may be made of any suitable material such as medical grade polyolefins, fluoropolymers, or polyvinylidene fluoride. The current thinking is that in order to transmit microwave energy in small diameter environments the wave guide should be a coaxial cable. Therefore, a coaxial wave guide is selected that is suitable for transmitting microwave energy. A suitable wave guide is the AS450-3050 coaxial cable supplied by Cooner of Chatsworth (Calif.). Of course, the diameter of the coaxial transmission line 53 will vary depending upon the needs of a particular system. However, generally, the larger the diameter, the better the microwave transmission characteristics will be. By way of example, as indicated above, in coronary applications, the catheter diameter is typically limited to approximately 7½ French (approximately 2.5 mm in diameter). In such a system, a wave guide that is approximately one meter long and has a diameter of 72 thousandths of an inch (1.8 mm) works well. The stiffener wire 58 may also represent a mechanical flexure device allowing for flexure control and improved steering.

An antenna 56 is provided at the distal end of the transmission line. Although the geometry of the antenna may vary in accordance with the needs of a particular application, a helical coil type antenna having a total length (i.e. length of the wire along the coil as opposed to the longitudinal length of the coil) equal to either one eighth or one quarter of the wavelength of the transmitted microwave energy has been found to work particularly well when the goal is to develop a strong field to the side of the antenna, which is desirable for certain applications. (This antenna configuration also exhibits particularly good coupling to the transmission line.) In view of this characteristic, the optimal actual length of such an antenna will vary in accordance with the selected frequency. The characteristics of the helical coil type antenna are the result of a variety of characteristics including shield (ground plane) to antenna gap, coil pitch, wire size and coil diameter. Although the interrelationship of these characteristics are not fully understood, the applicants have found that an antenna having a total wire length equal to one eighth of the wavelength, a wire diameter of 0.25 mm, a coil diameter of 1.47 mm, a pitch of 0.46 mm, and a shield to antenna (first coil) gap length of 1.47 mm works well.

It should be appreciated that the actual antenna geometry can be varied widely in accordance with the type of ablation that is desired for a particular application. For example, the helical antenna shown is particularly good at developing a strong electromagnetic field to the side of the catheter tip. On the other hand, a straight antenna tip that extends slightly beyond a shield may be more effective at developing fields that extend from the distal end of the catheter.

As seen in FIG. 7, a series of four electrodes 67–70 are provided at the tip of the catheter. The electrodes are provided for monitoring the patient's condition and/or the nature of the ablation process. In the described embodiment, the information obtained from the electrodes 67–70 is not used for the power supply, but rather is supplied to external electronics via connector 72 which is shown in FIG. 4. In alternative embodiments, some of the external electronics could be incorporated into the power supply and/or the power supply could use information obtained from the electrodes in its control scheme.

A shield 78 is positioned behind the antenna with the various electrodes and metallic wires being located behind the shield. Thus, the shield serves as an electromagnetic shield for the electronics. The distal end of the thermometry element 65 are positioned back from the distal edge of a shield 78. The electrodes 67–70 (electrode 70 is not shown) are positioned proximally relative to the antenna. Similarly, the distal end of stiffening wire 58 is positioned proximally relative to the shield. The reason for the positioning of the thermocouple, the electrodes and the stiffening wire behind the shield is to prevent their interference with the electromagnetic field and vice versa.

As seen in FIG. 7, a dielectric support 75 is coupled to the distal end of the coaxial transmission line 53 in the vicinity of the antenna 56. In the embodiment shown, the dielectric support has the helical antenna 56 wrapped thereabout. Since the field produced by the antenna is very intense on the coil's interior, it is important that the dielectric support material be capable of withstanding intense electromagnetic fields in the microwave frequency range. By way of example, a suitable dielectric material is Teflon, although other suitable materials could be used as well.

The tip of the catheter in the region of the antenna is insulated with a suitable insulation material 80 such as silicone or Teflon. By insulating the antenna 56, the described catheter avoids the charring and tissue destructing effects that are commonly experienced with exposed (uninsulated) catheter tips. Regardless of the type of microwave antenna used, the dangers of current induced charring caused by an uninsulated antenna may be overcome by insulating the antenna tip with a suitable dielectric material that is capable of withstanding the high energy field produced during use. Such insulation will eliminate all adverse current affects and will cause the abating process to be carried out solely on the basis of the electromagnetic fields that are generated. It is believed by the inventors that this insulating feature will become very important as the development of microwave catheters progresses. By eliminating the risks of charring, the risks of debris generation are virtually eliminated, temperature is controlled, and penetration is increased.

Although only one embodiment of the present invention has been described, it should be understood that the present invention may be embodied in many other specific forms without departing from the spirit or scope of the invention. Particularly, the invention has been described in terms of an ablation catheter for cardiac applications, however, it should be appreciated that the described small diameter microwave ablation catheter could be used for a wide variety of alternative applications as well. Further, the catheter design, the power supply design and the tuner design may all be modified within the scope of this invention. Therefore, the present examples are to be considered as illustrative and not restrictive, and the invention is not to be limited to the details given herein, but may be modified within the scope of the appended claims.

We claim:

1. A power supply for use in a microwave ablation catheter system that includes an ablation catheter having a waveguide that takes the form of a coaxial cable and an antenna carried by the waveguide, the ablation catheter being coupled to the power supply by a connector arrangement, the power supply comprising:
    a microwave energy generator for generating electromagnetic energy having a frequency in the microwave range, the microwave energy generator being coupled to the catheter waveguide through a coaxial transmission line and said connector;
    a reflected power monitor including a directional coupler in communication with one of said catheter waveguide and said transmission line, for diverting a small portion of the power that is reflected from the catheter during use, and a power sensor that monitors the magnitude of the power diverted by the directional coupler, the reflected power monitor being arranged to monitor the amount of power that is reflected from the catheter during use and outputting a signal indicative of the reflected power; and
    a tuner in communication with one of said transmission line, said catheter waveguide and said antenna, the tuner being arranged to facilitate matching the impedance of a power generator side portion of the catheter system with the impedance of a catheter side portion of the catheter system; and
    whereby the output signal indicative of the reflected power is available for use in adjusting the tuner to minimize reflected power.

2. A power supply as recited in claim 1 wherein:
    the tuner includes a manually adjustable control knob that can be accessed by a user to manually adjust the impedance of the catheter side portion of the catheter system; and
    the reflected power monitor further includes a display for displaying an indicia indicative of the reflected power to the user to facilitate manual adjustment of the control knob, the indicia being based at least in part on the output signal.

3. A power supply as recited in claim 1 wherein:
    the tuner automatically matches the impedance of the power generator side portion of the catheter system with a catheter side portion of the catheter system; and
    the tuner further includes a tuner controller that receives the signal indicative of the reflected power from the reflected power monitor and generates a control signal based at least in part on the signal indicative of the reflected power.

4. A power supply as recited in claim 1 wherein tuner includes a stub tuner coupled to the transmission line for impedance matching of the power supply portion of the catheter system to the catheter side portion of the catheter system.

5. A power supply as recited in claim 1 further comprising an interlock system for automatically shutting off the microwave energy generator when certain predefined safety hazards are detected.

6. A power supply as recited in claim 5 wherein the interlock system shuts off the energy generator when no catheter is plugged into the power supply.

7. A power supply as recited in claim 5 for use in an ablation catheter system having means for monitoring the temperature in the region of the, catheter tip, wherein the interlock system shuts off the microwave energy generator when an inappropriate thermal temperature is detected in the region of the catheter tip.

8. A power supply as recited in claim 5, wherein the interlock system shuts off the microwave generator when an abnormal increase in reflected power is detected by the reflected power monitor.

9. A power supply as recited in claim 5 wherein the interlock system shuts off the microwave generator when a short or an open circuit is detected in an electrical component.

10. A power supply as recited in claim 1 further comprising a display that receives said signal for providing the user with an indication of the magnitude of the reflected power.

11. A power supply as recited in claim 1 further comprising a transmitted power monitor for monitoring the amount of power transmitted to the catheter during use.

12. A power supply for use in a medical microwave ablation catheter system that includes an ablation catheter having a coaxial transmission waveguide and an antenna coupled to the coaxial transmission waveguide for radiating microwave energy, the coaxial transmission waveguide being coupled to the power supply by a connector arrangement, the power supply comprising:
    a microwave generator for generating electromagnetic energy having a frequency in the microwave range, the microwave energy generator being coupled to the coaxial transmission waveguide through a coaxial power supply transmission line and said connector;
    means for monitoring the amount of power that is transmitted to and reflected from the catheter during use, the monitoring means including,
    a first directional coupler in communication with the transmission line for diverting a small portion of the power that is reflected frown the catheter during use,
    a first power sensor for detecting the magnitude of the power diverted by the first directional coupler and outputting a first signal indicative of the magnitude of the power that is reflected from the catheter during use,
    a second directional coupler in communication with the transmission line for diverting a small portion of the power that is transmitted to the catheter during use,
    a second power sensor for detecting the magnitude of the power diverted by the second directional coupler and outputting a second signal indicative of the magnitude of the power that is transmitted to the catheter during use;
    means for detecting the temperature in the vicinity of the antenna portion of the ablation catheter;
    tuner means arranged to automatically match the impedance of a power generator side portion of the catheter system with the impedance of a catheter side portion of the catheter system, the tuning means including, a tuner controller that receives said first and second signals and generates a control signal based at least in part on the magnitude of the reflected power, and a stub tuning mechanism coupled to the transmission line for adjusting the impedance of the transmission line, the stub tuning mechanism being responsive to said control signal, and whereby the tuning means is arranged to match the impedance of the power generator side portion of the catheter system with the impedance of the catheter side portion of the catheter system at least in part by using the stub tuning mechanism to alter tile effective impedance of the transmission line; and an interlock system for automatically shutting off the microwave generator when certain predefined safety hazards are detected, the predetermined safety hazards including when no catheter is plugged into the power supply and when an over temperature condition is detected the interlock system being in communication with the temperature detecting means.

* * * * *